(12) United States Patent
Wolf et al.

(10) Patent No.: US 10,468,697 B2
(45) Date of Patent: Nov. 5, 2019

(54) ALCOHOL DETECTING FUEL CELL

(71) Applicant: ALCOTEK, INC., St. Louis, MO (US)

(72) Inventors: Karl R. Wolf, Eureka, MO (US); Joe Fodor, Fenton, MO (US)

(73) Assignee: Alcotek, Inc., St. Louis, MO (US)

( * ) Notice: Subject to any disclaimer, the term of this patent is extended or adjusted under 35 U.S.C. 154(b) by 0 days.

(21) Appl. No.: 16/149,791

(22) Filed: Oct. 2, 2018

(65) Prior Publication Data

US 2019/0036136 A1    Jan. 31, 2019

Related U.S. Application Data

(63) Continuation-in-part of application No. 15/254,854, filed on Sep. 1, 2016, now Pat. No. 10,090,542, which is a continuation of application No. 14/444,448, filed on Jul. 28, 2014, now Pat. No. 9,453,834.

(60) Provisional application No. 61/858,955, filed on Jul. 26, 2013.

(51) Int. Cl.
| | |
|---|---|
| *H01M 8/04* | (2016.01) |
| *H01M 8/04276* | (2016.01) |
| *H01M 16/00* | (2006.01) |
| *G01N 27/404* | (2006.01) |
| *H01M 4/92* | (2006.01) |
| *H01M 8/0247* | (2016.01) |
| *H01M 8/0239* | (2016.01) |
| *G01N 33/497* | (2006.01) |

(52) U.S. Cl.
CPC .... *H01M 8/04276* (2013.01); *G01N 27/4045* (2013.01); *G01N 33/4972* (2013.01); *H01M 4/92* (2013.01); *H01M 8/0239* (2013.01); *H01M 8/0247* (2013.01); *H01M 16/003* (2013.01); *H01M 2250/30* (2013.01); *Y02B 90/18* (2013.01); *Y10T 29/49108* (2015.01)

(58) Field of Classification Search
None
See application file for complete search history.

(56) References Cited

U.S. PATENT DOCUMENTS

| | | |
|---|---|---|
| 4,035,551 A | 7/1977 | Grevstad |
| 5,302,274 A | 4/1994 | Tomantschger et al. |
| 5,395,507 A | 3/1995 | Aston et al. |

(Continued)

OTHER PUBLICATIONS

International Search Report, International Patent Application No. PCT/US2014/048445, dated Nov. 7, 2014, 11 pages.

*Primary Examiner* — Wyatt P McConnell
(74) *Attorney, Agent, or Firm* — Lewis Rice LLC

(57) ABSTRACT

A new method of manufacturing a fuel cell, particularly for use in a breath alcohol detector, and the fuel cell created by the method. The fuel cell is constructed in two pieces, a mounting chip comprising a porous uncompressed substrate and an active element designed to fit within the mounting chip. Constructed in this way, electrolyte can flow from the mounting chip into the active element via near perfect capillary action to keep the electrode substrate full of electrolyte for long periods of time, increasing its useful life, especially under harsh conditions. Further, the capillary action need not work through a layer of electrode. Wire connections and arrangements are generally of no concern in this design as the reservoirs for electrolyte connect directly to the substrate and electrolyte does not need to pass through an electrode.

17 Claims, 5 Drawing Sheets

(56) References Cited

U.S. PATENT DOCUMENTS

| | | | |
|---|---|---|---|
| 5,830,337 A | 11/1998 | Xu | |
| 5,980,709 A * | 11/1999 | Hodges | G01N 27/30 204/403.06 |
| 5,985,675 A | 11/1999 | Charm et al. | |
| 7,022,213 B1 | 4/2006 | Austen et al. | |
| 7,534,333 B2 | 5/2009 | Khalafpour et al. | |
| 2006/0142651 A1 | 6/2006 | Brister et al. | |
| 2007/0072048 A1 | 3/2007 | Hongo et al. | |
| 2007/0154765 A1 | 7/2007 | Bayer et al. | |
| 2009/0194417 A1 | 8/2009 | King | |
| 2010/0190089 A1 | 7/2010 | Akiyama | |
| 2013/0101919 A1 | 4/2013 | Hiraiwa et al. | |

\* cited by examiner

ALCOHOL DETECTING FUEL CELL

CROSS REFERENCE TO RELATED APPLICATION(S)

This application is a Continuation-in-Part of U.S. application Ser. No. 15/254,854, filed Sep. 1, 2016, which is a Continuation of U.S. patent application Ser. No. 14/444,448, filed Jul. 28, 2014 and now U.S. Pat. No. 9,453,834, which in turn claims benefit of U.S. Provisional Patent Application Ser. No. 61/858,955, filed Jul. 26, 2013 and now expired. The entire disclosure of all the above documents is herein incorporated by reference.

BACKGROUND

1. Field of the Invention

Described herein is a fuel cell that includes a reservoir for electrolyte and a method for constructing said fuel cell. Specifically, the fuel cell may include one or more "sponge reservoirs" which comprise a portion of a porous substrate which is uncompressed and in fluid communication with the substrate which is compressed between electrodes.

2. Description of the Related Art

For the purposes of public safety on the roads and elsewhere, there is a need to make sure that individuals are not operating potentially dangerous machines (such as automobiles) while they are impaired by the effects of alcohol consumption. To try and prevent people from driving drunk, most states have enacted laws that impose fines or other criminal penalties if individuals have a breath or blood alcohol level above a certain amount. In order to effectively enforce these laws, it is necessary to be able to measure the alcohol concentration in human breath and compare the results against legal limits. There are a variety of measuring instruments used for determining the concentration of alcohol in human breath ranging from small hand held devices to larger bench top units and machines built into cars or certain machinery. Since a determination of breath alcohol above the legal threshold can result in criminal penalties, loss of a job, or other sanctions, the accuracy of these instruments is paramount.

Fuel cells which are being used as sensors, and particularly fuel cells as alcohol sensors such as may be used in breath alcohol sensors, have typically had the active element constructed as shown in FIG. 1. This sensor (100) is typically manufactured by arranging the components and then compressing the sensor (100) under pressure in order to get the material of the electrodes (101), generally platinum, to adhere to the substrate (103). In the process, the porous substrate (103) is typically permanently deformed resulting in a smaller effective pore size of the substrate compared to its pore size prior to pressing. It is these pores of the substrate (103) that hold liquid electrolyte to allow the sensor (100) to function and the pores are typically filled by soaking the sensor (100) after pressing. Once filled with liquid electrolyte, the sensor (100) can act as a fuel cell.

Typical electrode assemblies might be round or square as shown in FIG. 2 and are typically less than 1 mm thick. Substrates (103) are generally a porous material such as, but not limited to, porous PVC and porous polypropylene, but there are many candidate materials. Those skilled in the art will understand that these sensors (100) are, therefore, generally very small and therefore typically will hold a very small amount of electrolyte. Five one-hundredths (0.05) of a milliliter would not be an unusual quantity.

Fuel cell sensors in portable equipment, such as those used by highway patrol officers, by definition, must operate in a variety of ambient conditions such as hot, cold, humid, and arid environments. Hot and/or arid conditions tend to draw water out of the fuel cell electrolyte as the water in the electrolyte tries to reach equilibrium with the environment. Even if the electrode sensor (100) is enclosed in a case (300), water can be drawn out through the case material, which is rarely completely air and fluid sealed, or through necessary sampling ports (301) allowing the sensor (100) to be used in the breath alcohol sensor as is shown in FIG. 3. Previously attempted remedies against water loss generally add cost and complexity and are not 100% effective, especially over an expected sensor life in the marketplace measured in years, and especially in a punishing environment.

In some cases, sensors (100) are used in indoor bench top equipment. Although this is typically a moderated environment compared to the great outdoors, indoor conditions can still be quite arid, especially in winter. Sensors (100) are also often heated in bench top equipment for measuring reasons, generally making the fuel cell microenvironment even drier than the overall room conditions.

Those skilled in the art will understand that if all the water, or nearly all the water, is drawn out of an assembly's (100) electrolyte, the sensor (100) will cease to work and may become permanently damaged. Various degrees of water loss short of 100%, or nearly 100%, typically do not keep an assembly (100) from measuring accurately. However, the response time may become slower, for example.

Over the years, a variety of methods have been used to deal with electrolyte water loss. In one example where the gas sample is human breath (which is common in a breath alcohol detector), every time a sample is taken, moisture will be added to the substrate (103) from humidity in the breath as shown in FIG. 4. However, the amount of moisture added per sample is generally so small, and the typical number of tests run on an instrument over a year is also small enough that these additive effects are typically swamped by the opposite effect of water loss.

Humid ambient conditions (which result in less water loss and possibly even water gain through the inverse of the above processes) are more likely to be the driving force behind water gain in a fuel cell than breath addition. A sensor (100) containing an electrolyte can take on water from very humid ambient conditions. The paths of water gain from the ambient are the same as water loss to the ambient, only in reverse. Those skilled in the art will understand that, while this can be beneficial, if the sensor substrate (103) is already saturated with liquid, it may continue to take on liquid from the humid ambient conditions until the volume of such liquid exceeds the designed containment capacity of the sensor (100). In this case, liquid can overflow the sensor (100) and appear on the electrode (101) surfaces or other locations where it will likely hinder the intended operation of the sensor (100).

Certain fuel cell designs have allowed manufacturers to experiment with manually adding drops of water directly to an exposed electrode (101) (anode) of the sensor (100) when it has dried out significantly as shown in FIG. 5. Results have been mixed as water loss often causes the assembly (100) to reach a tipping point where adding water back does not reverse the effects of losing it in the first place. Further, at times, the drier platinum electrode (101) becomes partially hydrophobic and the added liquid can take considerable time to soak in, if it can at all. Thus, addition via the anode side of the sensor (100) is often ineffective.

It is generally believed that the ideal electrolyte situation is to constantly keep the substrate (103) filled from the very beginning of the sensor's (100) useful life. For many years, some fuel cell sensor (100) manufacturers have been adding "backup" disks (107) in the construction of fuel cell sensor (100) assemblies. This is an extra disk of substrate without an attached electrode that is typically assembled behind the cathode (101). The backup disk (107) has typically been made of the same substrate material as the electrode disk (103), but without any compression, leaving the pores in their original state. Therefore, this disk (107) will hold more electrolyte than the pressed version.

The backup disk (107) acts as a reservoir for extra electrolyte to replenish the electrolyte in the substrate (103) between the electrodes (101) when water is lost to ambient conditions. The smaller (compressed) pores of the substrate (103) between the electrodes (101) preferentially stays full compared to the backup disk (107) due to capillary action since the backup disk (107) pores are larger. FIG. 6 provides an embodiment of such a backup disk (107).

This solution has worked reasonably well in the field in many instances. There are a couple of drawbacks with this construction, however. The complete fuel cell sensor (100) generally includes wires (111) to connect the electrode (101) surfaces to an external circuit (109) for measuring the current produced from a gas sample. This construction typically places a wire (111) between one electrode surface (101) and the backup disk (107) which to some degree prevents a perfect contact surface between electrode (101) and backup disk (107) as shown in FIG. 7. Thus, the capillary action is somewhat hindered between the backup disk (107) and the substrate (103). Also, as mentioned above, the electrode (101) surface itself presents an additional layer through which the moisture must travel and may detract from an ideal capillary action.

As a final note, there is no good way to tell whether a sensor (100) is flush with electrolyte or starved for electrolyte unless or until a large degradation in performance becomes apparent. By the time this happens, it is often too late to reverse that degradation by adding water or electrolyte and the sensor (100) is effectively destroyed.

SUMMARY

The following is a summary of the invention in order to provide a basic understanding of some aspects of the invention. This summary is not intended to identify key or critical elements of the invention or to delineate the scope of the invention. The sole purpose of this section is to present some concepts of the invention in a simplified form as a prelude to the more detailed description that is presented later.

Because of the above-described issues and other problems in the art, described herein is method for forming a fuel cell that includes a reservoir for electrolyte, and a new design for said fuel cell. Specifically, the fuel cell may include one or more "sponge reservoirs" which comprise a portion of the porous substrate which is uncompressed and in generally continuous fluid communication with a portion of the substrate which is compressed between the electrodes. The fuel cell may also include one or more liquid reservoirs in generally continuous fluid communication with the sponge reservoirs. The fuel cell is generally constructed by compressing an uncompressed porous substrate between two electrodes to from an active element. The active element is then placed in a counterbored hole in a mounting chip comprising an uncompressed porous substrate, with the counterbored hole's size, shape, and depth customized to ensure fluid communication between the uncompressed porous substrate of the mounting chip and the compressed porous substrate of the active element. So formed, the mounting chip provides a fluid reservoir for the active element.

There is described herein, in an embodiment, a method of forming a fuel cell, the method comprising: providing at least one active element, each comprising at least two electrodes, and a porous compressed substrate, wherein a first of said at least two electrodes is arranged on a first side of said porous compressed substrate, and wherein a second of said at least two electrodes is arranged on a second side of said porous compressed portion; machining a mounting chip comprising a porous uncompressed substrate with at least one counterbore hole, each said at least one counterbore hole being formed with a depth equal or greater than the height of a corresponding active element of said at least one active elements, said at least one counterbore hole being formed with a size and shape to allow fluid communication of electrolyte from said mounting chip to said active element when said corresponding active element is disposed within a corresponding counterbore hole of said at least one counterbore hole; and placing in each said at least one counterbore hole within said mounting chip said corresponding active element of said at least one active elements.

In one embodiment of the method, the machining step further comprises drilling at least one drilled hole, said at least one drilled hole extending from the depth of the at least one counterbore hole through the mounting chip.

There is also described herein, among other things, a fuel cell comprising: at least one active element, each comprising at least two electrodes, and a porous compressed substrate, wherein a first of said at least two electrodes is arranged on a first side of said porous compressed substrate, and wherein a second of said at least two electrodes is arranged on a second side of said porous compressed portion; and a mounting chip comprising: a porous uncompressed substrate with at least one counterbore hole, wherein each said at least one counterbore hole is formed with a depth equal or greater than the height of a corresponding active element of said at least one active element; and wherein said at least one counterbore hole is formed with a size and shape to allow fluid communication of electrolyte from said mounting chip to said active element when said corresponding active element is disposed within a corresponding counterbore hole of said at least one counterbore hole.

In an embodiment, the fuel cell further comprises an encapsulating housing.

In an embodiment of the fuel cell, the housing includes at least one liquid reservoir in fluid communication with said mounting chip.

In an embodiment of the fuel cell, the at least one liquid reservoir comprises at least three liquid reservoirs, said at least three liquid reservoirs being positioned so that liquid in at least one of said at least three reservoirs contacts said mounting chip regardless of orientation of said fuel cell.

In an embodiment of the fuel cell, the electrodes comprise platinum.

In an embodiment of the fuel cell, the fuel cell is used in a breath alcohol sensor.

In an embodiment of the fuel cell, the porous compressed substrate comprises porous polypropylene.

In an embodiment of the fuel cell, the porous compressed substrate comprises porous polyvinylchloride (PVC).

In an embodiment of the fuel cell, the porous uncompressed substrate comprises porous polypropylene.

In an embodiment of the fuel cell, the porous uncompressed substrate comprises porous polyvinylchloride (PVC).

In an embodiment of the fuel cell, the pores in said porous compressed substrate include a liquid electrolyte.

In an embodiment of the fuel cell, the pores in said porous uncompressed substrate include a liquid electrolyte.

In an embodiment of the fuel cell, the electrodes are circular.

In an embodiment of the fuel cell, the porous compressed substrate is polygonal.

In an embodiment of the fuel cell, said at least one counterbore hole contains at least one drilled hole, said at least one drilled hole extending from the depth of the counterbore hole through the mounting chip.

DESCRIPTION OF THE PREFERRED EMBODIMENT(S)

Because of the above-described issues and other problems in the art, described herein is method for forming a fuel cell that includes a reservoir for electrolyte, and a new design for said fuel cell. This new design, formed in two pieces, allows for a mounting chip to serve as a reservoir for extra electrolyte that passes between the uncompressed porous substrate of the mounting chip to the compressed porous substrate of the active element, allowing for near perfect capillary action to keep the active element full of electrolyte for long periods of time. This can increase its useful life, especially under harsh conditions. Further, the capillary action need not work through a layer of electrode and can be integrally formed with the electrode element to eliminate or reduce loss due to connective surfaces. Wire connections and arrangements are generally of no concern in this design as the reservoirs for electrolyte connect directly to the substrate and electrolyte does not need to pass through an electrode.

Figure 11:
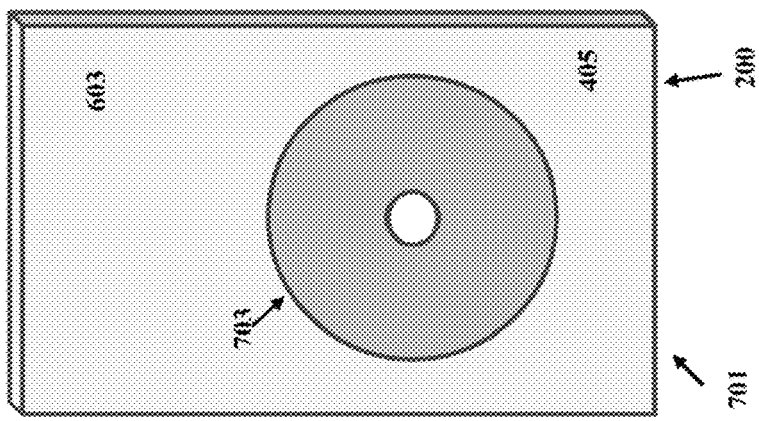
FIG. 11 shows a top-down view of an embodiment of a completed fuel cell, with an active element placed within the counterbored hole of the mounting chip
Figure 9:
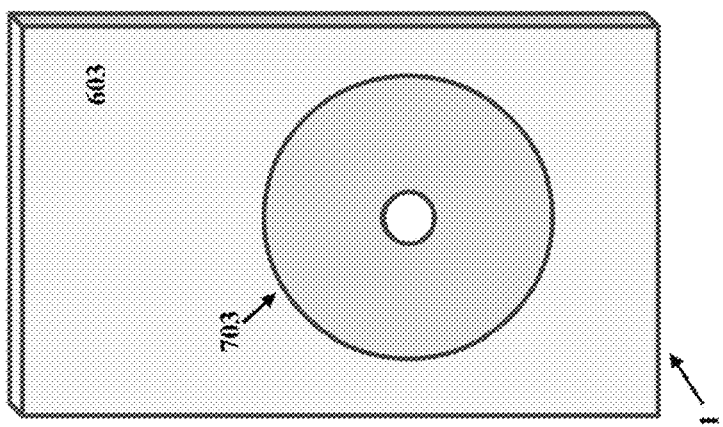
FIG. 9 shows a three-dimensional top-down view of a mounting chip with a counterbored hole.
Figure 8:
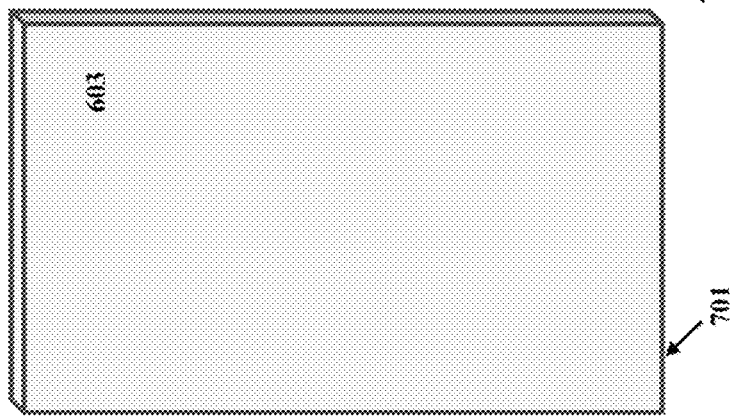
FIG. 8 shows a three-dimensional top-down view of a mounting chip without a counterbored hole.
Figure 10:
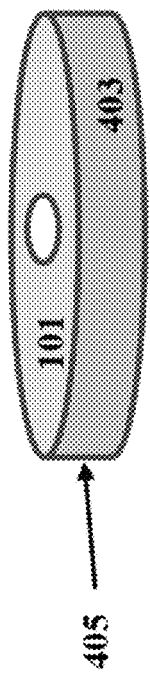
FIG. 10 shows a three-dimensional side-on view of an active element shaped to fit within the counterbored hole of the mounting chip, allowing for generally continuous lateral fluid communication of electrolyte between the compressed porous substrate of the active element and the uncompressed porous substrate of the mounting chip.
Figure 12:
FIG. 12 shows a two-dimensional side-on view of a mounting chip without a counterbored hole.
Figure 13:
FIG. 13 shows a two-dimensional side-on view of a mounting chip with a counterbored hole and a two-dimensional side-on view of an active element shaped to fit within the mounting chip, allowing for generally continuous lateral fluid communication of electrolyte between the compressed porous substrate of the active element and the uncompressed porous substrate of the mounting chip.
Figure 13:
Figure 14:
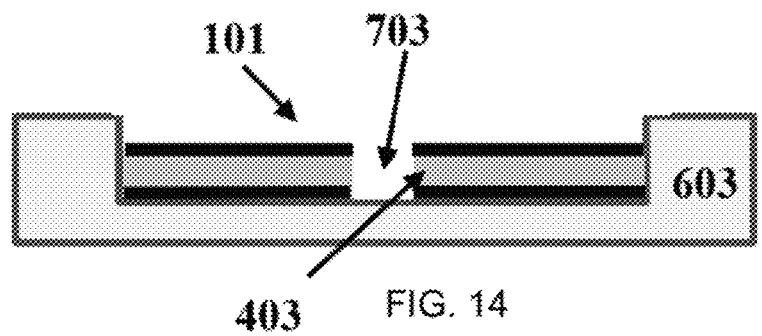
FIG. 14 shows a two-dimensional side-on view of one embodiment of a completed fuel cell, with an active element placed within the counterbored hole of the mounting chip such that a thickness of uncompressed porous substrate remains beneath the active element.

FIGS. 8-15 provide a first embodiment of a method of forming a fuel cell (200), beginning in FIGS. 8 and 12 with a mounting chip (701) comprising a solid piece of uncompressed porous substrate (603). A counterbored hole (703) is machined into the mounting chip (701) as shown in FIGS. 9 and 13, preferably to a depth equal or greater than the height of the active element (405), and in a size and shape to allow generally continuous fluid communication of electrolyte laterally between the uncompressed porous substrate (603) of the mounting chip (701) and the compressed porous substrate (403) of the active element (405), when the active element (405) is disposed within the counterbored hole (703), as shown in FIGS. 9, 10, and 13. FIGS. 11 and 14 shows a top-down and a side-on view, respectively of the completed fuel cell, with the active element allowing for fluid communication with the mounting chip.

The mounting chip (701) may be counterbored in any manner understood from one of ordinary skill in the art, preferably to a depth equal or greater than the height of the active element (405), and in a size and shape to allow generally continuous fluid communication of electrolyte laterally between the uncompressed porous substrate (603) of the mounting chip (701) to the porous compressed substrate (403) of the active element (405).

As depicted in FIG. 8, the mounting chip (701) is shown as comprising a solid piece of uncompressed porous substrate (603) roughly rectangular in shape, but the specific size and shape of the mounting chip (701) is not critical to the invention.

Moreover, while the exact types of uncompressed porous substrate (603) and compressed porous substrate (403) are not critical to the invention, the substrates generally will be porous and will generally be composed of traditional materials, such as, but not limited to, porous PVC or porous polypropylene. Further, the material chosen for the uncompressed porous substrate (603) and compressed porous substrate (403) will generally be the same.

Further, the exact type of electrolyte used is also not critical, but the electrolyte will generally be liquid or in suspension or solution.

As depicted most readily in FIG. 10, the active element (405) is shown as a right circular open cylinder, but the specific size, shape, and height of the active element (405) is not critical to the invention, so long as the size, shape, and height of the active element (405) allows it to be placed within the counterbored hole (703) to allow generally continuous fluid communication of electrolyte laterally between the uncompressed porous substrate (603) of the mounting chip (701) and the compressed porous substrate (403) of the active element (405), when the active element (405) is disposed within the counterbored hole (703), as shown in FIGS. 11 and 14.

Similarly, as depicted in FIG. 9, a counterbored hole (703) is shown as roughly circular in shape, but the specific size, shape, and depth of the counterbored hole (703) is not critical to the invention, so long as the counterbored hole (703) is machined into the mounting chip (701) preferably to a depth greater than the thickness of the active element (405), and to a size and shape to allow generally continuous fluid communication of electrolyte laterally between the uncompressed porous substrate (603) of the mounting chip (701) and the compressed porous substrate (403) of the active element (405), when the active element (405) is disposed within the counterbored hole (703), as shown in FIGS. 11 and 14.

Finally, as shown in the embodiment depicted in FIG. 14, the active element (405) is shown to be with a thickness less than that of the mounting chip (701), resulting in a certain thickness of uncompressed porous substrate beneath the electrode layer (101) of the active element (405). The embodiment also shows the electrode layer (101) at a level beneath the top surface of the mounting chip (701).

Figure 15:
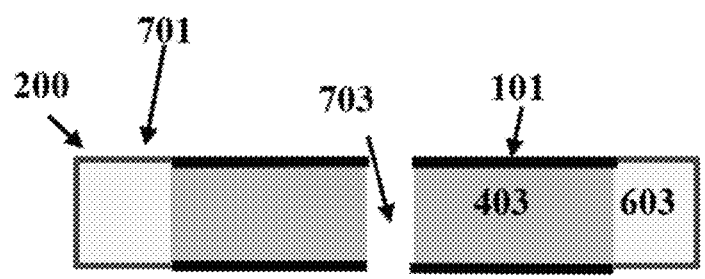
FIG. 15 shows a two-dimensional side-on view of a different embodiment of a completed fuel cell, with the top and bottom surfaces of the active element flush with the top and bottom surfaces of the mounting chip.

However, having an active element with electrode layers interior to the surfaces of the mounting chip (701) or even having an active element (405) with a thickness of less than that of mounting chip (701) is not critical to the invention as the active element (405) can be as thick or thicker than the mounting chip (701), with the counterbored hole extending through the entire thickness of the mounting chip (701), resulting in a fuel cell (200) where the electrode layers (101) are flush with the top and bottom surface of the mounting chip (701), as shown in FIG. 15, where the size and shape of the counterbored hole (703) within the mounting chip (701) keeps the active element (405) in place via friction fit or some other means apparent to one of ordinary skill.

As would be apparent to one of ordinary skill, all of the above variations are within the discretion of the designer depending on the sum of all the factors that influence the forming of the active element (405), the mounting chip (701), and the counterbored hole (703) for the fuel cell (200). There may be numerous variations along these lines without changing the nature of the invention.

The combination of the mounting chip (701) with counterbored hole (703) and the active element (405), with the uncompressed porous substrate (603) of the mounting chip in direct contact with the compressed porous substrate (403) of the active element, allowing for generally continuous fluid communication of electrolyte laterally between the uncompressed porous substrate (603) and the compressed porous substrate (403) constitutes the fuel cell (200). Construction via this method allows for removal and replacement of an active element (405), or the replacement of a mounting chip (701) without sacrificing the entire fuel cell (200).

In a further embodiment of the method, the machining step of the one or more additional drilled holes from the top surface of the counterbored hole (703) through the uncompressed porous substrate (603) of the mounting chip (701).

Also described herein is a fuel cell (200), formed according to the method described herein, with one possible embodiment depicted in FIG. 10, with an active element (405) placed in a counterbored hole (703) of a mounting chip (701) to allow generally continuous fluid communication of electrolyte laterally between the uncompressed porous substrate (603) of the mounting chip (701) and the compressed porous substrate (403) of the active element (405) when the active element (405) is disposed within the counterbored hole (703).

As described above, the precise size, shape, and depth of the counterbored hole (703), the manner in which the counterbored hole (703) is counterbored into the mounting chip (701), the precise size, shape, and thickness of the mounting chip (701), and the precise size, shape, and thickness of the active element (405) are not critical to the invention, provided that the size and shape of each of the counterbored hole (703), mounting chip (701) and active element (405) are such that the active element has a thickness preferably no greater than the depth of the counterbored hole (703), and that the dimensions of the counterbored hole (703), mounting chip (701) and active element (405) to allow generally continuous fluid communication of electrolyte laterally between the uncompressed porous substrate (603) of the mounting chip (701) and the compressed porous substrate (403) of the active element (405) when the active element (405) is disposed within the counterbored hole (703).

Additionally, while the exact types of uncompressed porous substrate (603) and compressed porous substrate (403) are not critical to the invention, the substrates generally will be porous and will generally be composed of traditional materials, such as, but not limited to, porous PVC or porous polypropylene. Further, the material chosen for the uncompressed porous substrate (603) and compressed porous substrate (403) will generally be the same.

The exact type of electrolyte used is also not critical, but the electrolyte will generally be liquid or in suspension or solution.

In a still further embodiment, the fuel cell (200) is placed within a case (400) which serves to further enhance access to liquid electrolyte. Specifically, there may be included one or more liquid reservoirs (401) that work with or in conjunction with the mounting chip substrate (701). Thus, there can be additional liquid electrolyte (401) that is in contact with the mounting chip substrate (701). An embodiment of such a case (400), with a fuel cell (200) therein, is provided in FIGS. 16 and 17. The liquid reservoirs (401) in this embodiment (there are 6) are part of the case (400) design and are analogous to a bottle of liquid electrolyte which is in fluid contact with the uncompressed porous substrate (603) of the mounting chip (701), whereas the uncompressed porous substrate (603) of the mounting chip (701) in the electrode discussed above is more analogous to a storage sponge and is in integral fluid communication with the compressed porous substrate (403) of the active element (405).

This aspect opens up the possibility of an easily refillable dual reservoir (sponge and liquid) system which could be monitored in various ways. By capillary action, the uncompressed porous substrate (603) of the mounting chip (701) would generally continuously take in liquid from the liquid reservoir (401) as needed to replenish any loss. Thus, the uncompressed porous substrate (603) of the mounting chip (701) would remain continuously full or at least full enough to supply compressed porous substrate (403) of the active element (405) so that it is always full even as the level of liquid in the liquid reservoirs (401) was depleted.

Figure 16:
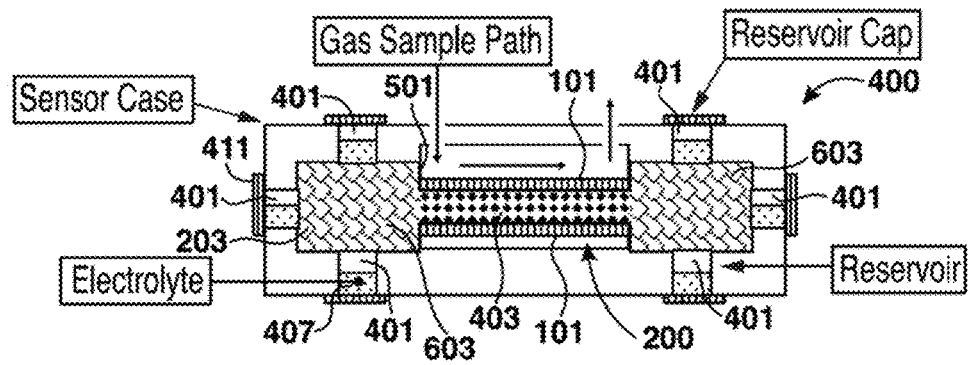
FIG. 16 shows a cross-sectional side view of a fuel cell of FIG. 15 inside a fuel cell housing with six liquid or "bottle" reservoirs.
Figure 17:
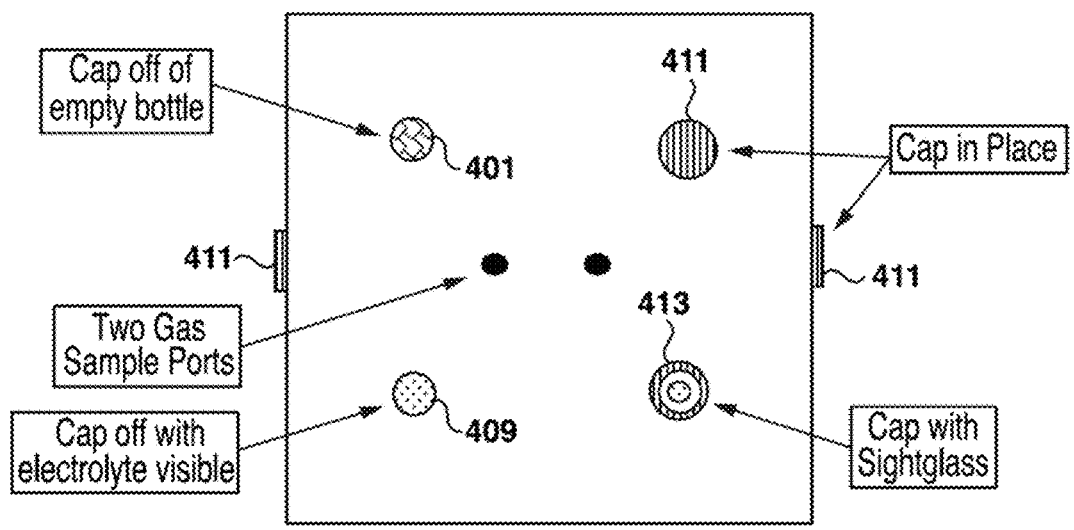
FIG. 17 shows a top-down view of a fuel cell case of FIG. 16 showing various caps and states of the various liquid reservoirs.

In order to provide liquid reservoirs (401), there could be a single "bottle" or there could be multiple "bottles" as shown in FIGS. 16 and 17. There could be "bottle(s)" on one side of the mounting chip (701) or multiple sides. Bottle(s) could be at the outer periphery of the mounting chip (701), i.e., in contact with the edge of the mounting chip (701) or along any surface including interior surfaces above the electrode (101) or even within the structure of the mounting chip (701). Having bottles in multiple locations as is shown in FIGS. 16 and 17 allows replenishment of the mounting chip (701) no matter the orientation of the fuel cell (200) and/or measuring instrument. In effect, electrolyte (409) will be pulled by gravity to be in contact with the mounting chip (701) regardless of orientation.

In the embodiment of FIGS. 16 and 17, the case (400) is constructed such that there is no bottom to the liquid reservoir (401). Instead, the mounting chip (701) serves as the bottom. It is highly undesirable for liquid electrolyte to contact the electrode (101) surface on the gas sample side of the electrode, as this will severely degrade the ability of the sensor to accurately measure any gas sample unless it is removed prior to taking a sample. Because of this, it may be necessary to seal off all or a portion of the mounting chip (701) surface from the exterior or from the electrode (101). For example, the surface (501) of the mounting chip (701) near the electrode (101) may be sealed in any manner understood from one of ordinary skill in the art to inhibit the mounting chip (701) from becoming overfilled and potentially "weeping" electrolyte onto the electrode (101) surface.

Figure 1:
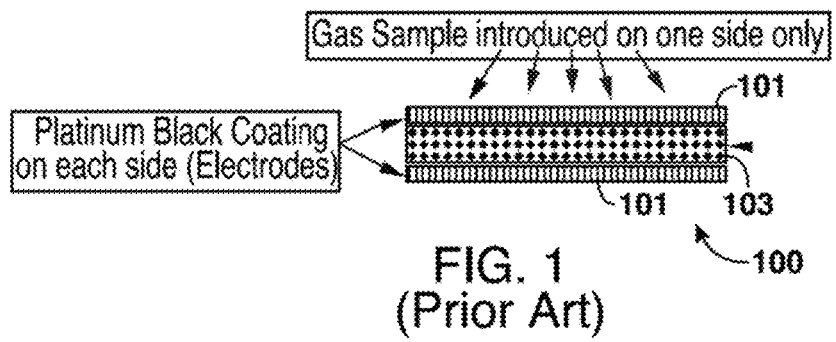
FIG. 1 shows an embodiment of a typical fuel cell of the prior art.
Figure 2:
FIG. 2 shows two embodiments of typical electrode shapes and sizes found in the prior art.
Figure 3:
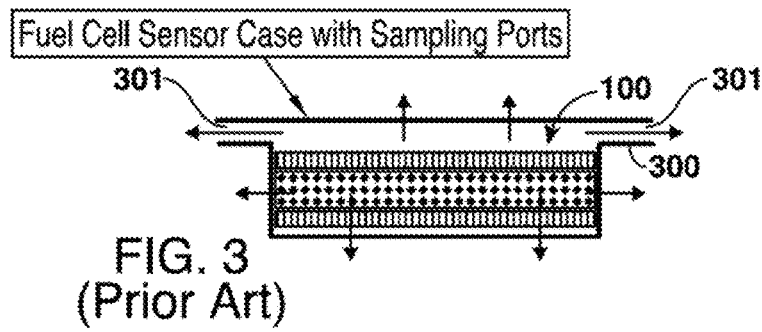
FIG. 3 shows various paths of liquid electrolyte water loss from a typical fuel cell including through sampling ports and a case body as found in the prior art.
Figure 4:
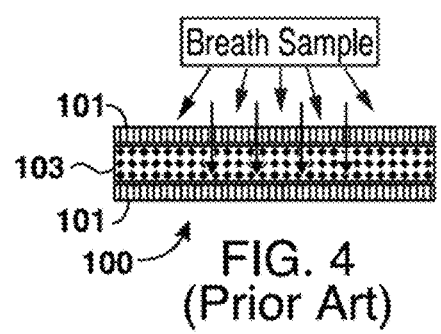
FIG. 4 shows potential recuperation of electrolyte water from humid breath samples of the prior art.
Figure 5:
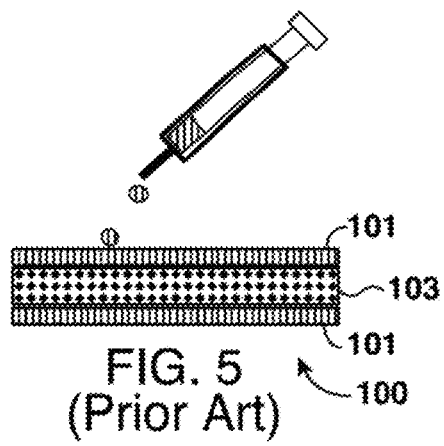
FIG. 5 shows a conceptual diagram of externally adding water to a fuel cell sensor of the prior art.
Figure 6:
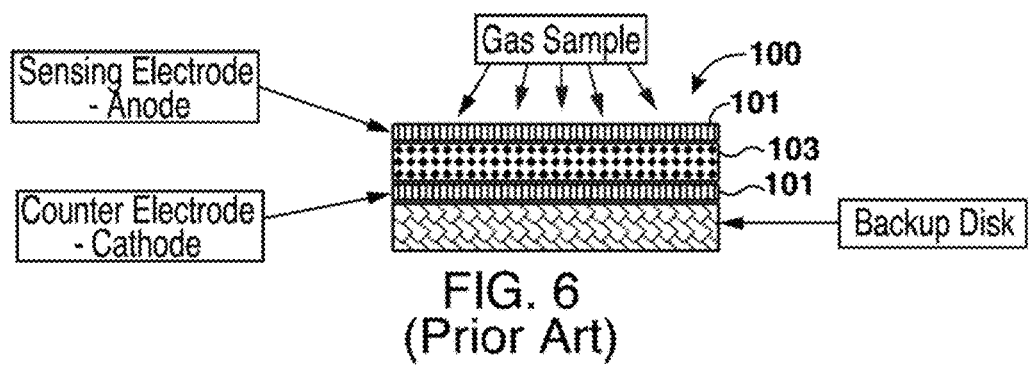
FIG. 6 shows an embodiment of a fuel cell sensor of the prior art with a backup substrate disk showing the capillary action taking electrolyte from the backup disk to the substrate.
Figure 7:
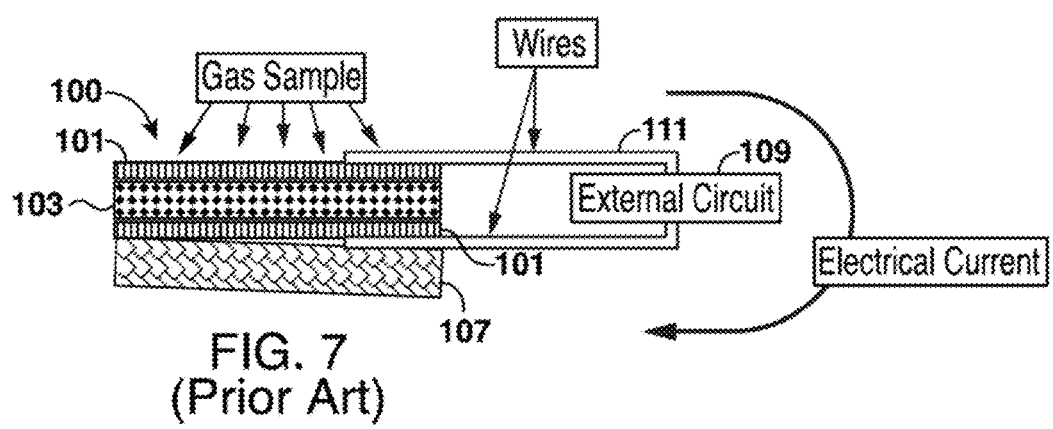
FIG. 7 shows an embodiment of a fuel cell sensor of the prior art with a backup disk showing the wires for the electrodes creating an imperfect connection with the backup disk.

In a still further embodiment, the capillary action of the mounting chip (701), if it was not full, can actually be used to pull liquid electrolyte from the electrode surface (101) to replenish its stock of electrolyte by allowing electrolyte to be placed on the electrode surface (101) as shown in FIG. 5 and then tilting the device of FIG. 16 to place surface (501) downward. Still further, the sponge action could similarly be used to pull fluid water or other fluids from the surface of the electrode (101).

Those skilled in the art will understand that the liquid reservoir(s) (401) can include caps (411) which could be removable for re-filling or not removable for a one-time fill. The caps (411) may, in an embodiment, be vented. Those skilled in the art will also understand that sensors of various types could be incorporated with the liquid reservoirs (401) and/or caps (411) to either visually or electronically monitor how full the liquid reservoirs (401) are, such as is shown in FIG. 17. Examples of such sensors could be a sight glass (413) or an electronic liquid level sensor. A single liquid reservoir (401) could hold many times the amount of electrolyte (409) held in the mounting chip (701) providing a large excess of electrolyte (409), but the exact amounts and proportions are at the discretion of the designer implementing the invention.

Those skilled in the art will understand the liquid reservoir (401) can be any shape and cover any amount of the mounting chip (701) surface. For example, a single liquid reservoir (401) could completely surround the entire edge perimeter of the mounting chip (701) as long as the electrolyte is maintained in the liquid reservoir (401) bottle or will enter the mounting chip substrate (701). Alternatively, the mounting chip (701) can be used alone without the liquid reservoir (401).

Conversely, an alternate embodiment of the invention has the liquid reservoir (401) only, attaching directly to the compressed substrate (403) of the active element (405).

Often, there is a desire to keep a fuel cell (200) small such as in portable equipment. Although the methods outlined above makes for a very compact design, there may be a desire to have a reservoir that could hold even more electrolyte without increasing the size by including liquid reservoirs (401) in the housing or case (400). In an embodiment of such a fuel cell (200), additional electrolyte storage can be accomplished by the choice of material used for the uncompressed porous substrate (603) and compressed porous substrate (403), depending on the nature of its pores in the compressed and uncompressed states, but differences in total reservoir volume with such design options may be marginal and may present other concerns.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A method of forming a fuel cell, the method comprising:
   providing at least one active element, each comprising:
      at least two electrodes; and
      a porous compressed substrate;
      wherein a first of said at least two electrodes is arranged on a first side of said porous compressed substrate; and
      wherein a second of said at least two electrodes is arranged on a second side of said porous compressed portion;
   machining a mounting chip comprising a porous uncompressed substrate with at least one counterbore hole, each said at least one counterbore hole being formed with a depth equal or greater than the height of a corresponding active element of said at least one active elements, said at least one counterbore hole being formed with a size and shape to allow fluid communication of electrolyte from said mounting chip to said active element when said corresponding active element is disposed within a corresponding counterbore hole of said at least one counterbore hole; and
   placing in each said at least one counterbore hole within said mounting chip said corresponding active element of said at least one active elements.

2. The method of claim 1, wherein the machining step further comprises drilling at least one drilled hole, said at least one drilled hole extending from the depth of the at least one counterbore hole through the mounting chip.

3. A fuel cell comprising:
   at least one active element, each comprising:
      at least two electrodes; and
      a porous compressed substrate;
      wherein a first of said at least two electrodes is arranged on a first side of said porous compressed substrate; and
      wherein a second of said at least two electrodes is arranged on a second side of said porous compressed portion; and a mounting chip comprising:
- a porous uncompressed substrate with at least one counterbore hole;
- wherein each said at least one counterbore hole is formed with a depth equal or greater than the height of a corresponding active element of said at least one active elements; and
- wherein said at least one counterbore hole is formed with a size and shape to allow fluid communication of electrolyte from said mounting chip to said active element when said corresponding active element is disposed within a corresponding counterbore hole of said at least one counterbore hole.

4. The fuel cell of claim 3 further comprising an encapsulating housing.

5. The fuel cell of claim 4 wherein said housing includes at least one liquid reservoir in fluid communication with said mounting chip.

6. The fuel cell of claim 5 wherein said at least one liquid reservoir comprises at least three liquid reservoirs, said at least three liquid reservoirs being positioned so that liquid in at least one of said at least three reservoirs contacts said mounting chip regardless of orientation of said fuel cell.

7. The fuel cell of claim 3 wherein said at least two electrodes comprise platinum.

8. The fuel cell of claim 3 wherein said fuel cell is used in a breath alcohol sensor.

9. The fuel cell of claim 3 wherein said porous compressed substrate comprises porous polypropylene.

10. The fuel cell of claim 3 wherein said porous compressed substrate comprises porous polyvinylchloride (PVC).

11. The fuel cell of claim 3 where said porous uncompressed substrate comprises porous polypropylene.

12. The fuel cell of claim 3 where said porous uncompressed substrate comprises porous polyvinylchloride (PVC).

13. The fuel cell of claim 3 wherein pores in said porous compressed substrate include a liquid electrolyte.

14. The fuel cell of claim 3 wherein pores in said porous uncompressed substrate include a liquid electrolyte.

15. The fuel cell of claim 3 wherein said electrodes are circular.

16. The fuel cell of claim 3 wherein said mounting chip is polygonal.

17. The fuel cell of claim 3 wherein one or more of said at least one counterbore hole contains at least one drilled hole, said at least one drilled hole extending from the depth of the counterbore hole through the mounting chip.

* * * * *